(12) United States Patent
Lacout et al.

(10) Patent No.: US 6,923,989 B2
(45) Date of Patent: Aug. 2, 2005

(54) METHOD FOR PREPARING A CALCIUM PHOSPHATE PASTY MATERIAL FOR INJECTION

(75) Inventors: Jean-Louis Lacout, Toulouse (FR); Michèle Freche, Fonsegrives-Quint (FR); Stephane Goncalves, Toulouse (FR); Fernand Rodriguez, Aureville (FR)

(73) Assignee: Ceravic, Vic en Bigorre (FR)

( * ) Notice: Subject to any disclaimer, the term of this patent is extended or adjusted under 35 U.S.C. 154(b) by 0 days.

(21) Appl. No.: 10/220,052

(22) PCT Filed: Feb. 27, 2001

(86) PCT No.: PCT/FR01/00563

§ 371 (c)(1),
(2), (4) Date: Aug. 27, 2002

(87) PCT Pub. No.: WO01/64260

PCT Pub. Date: Sep. 7, 2001

(65) Prior Publication Data

US 2003/0021824 A1 Jan. 30, 2003

(30) Foreign Application Priority Data

Mar. 1, 2000 (FR) .......................................... 00 02615

(51) Int. Cl.⁷ ...................... A61K 33/42; A61K 31/661; A61K 33/06; A61K 47/00
(52) U.S. Cl. ........................ 424/602; 424/422; 424/423; 424/601; 424/605; 424/682; 424/688; 424/694; 514/63; 514/75; 514/143; 514/769; 514/772

(58) Field of Search .................................. 424/422, 423, 424/601, 602, 605, 682, 688, 694; 514/63, 75, 143, 769, 772, 602, 605, 688

(56) References Cited

U.S. PATENT DOCUMENTS 5,522,893 A * 6/1996 Chow et al. ................. 423/305

FOREIGN PATENT DOCUMENTS

| EP | 0 276 836 | 8/1988 |
| EP | 0 684 046 | 11/1995 |
| FR | 2 776 282 | 9/1999 |

OTHER PUBLICATIONS

XP–002154942, JP62122670, Jun. 3, 1987.

* cited by examiner

*Primary Examiner*—S. Mark Clardy
*Assistant Examiner*—Frank Choi
(74) *Attorney, Agent, or Firm*—Young & Thompson

(57) ABSTRACT

A method for preparing a calcium phosphate pasty material for injection which after, setting, is designed to form an apatite material consists in: producing from water and calcium phosphates pasty mixture capable of developing, hardening and forming a hydroxyapatite. The method is characterised in that it consists in adding to the calcic phosphates or to the pasty mixture before it is injected a methicone having relative to the mixture more than 0.30 wt. % and less than 10 wt. %. The resulting material can be injected, that is it can be transported in pasty form into a conduit under moderate pressure levels. The material sets on the site of implantation and hardens to form an apatite biomaterial in a manner similar to known methicone-free calcium phosphate mixtures.

11 Claims, 3 Drawing Sheets

METHOD FOR PREPARING A CALCIUM PHOSPHATE PASTY MATERIAL FOR INJECTION

The invention relates to a process for the preparation of an injectable pasty material from a mixture of water and calcium phosphates which is capable of developing, hardening and forming a hydroxyapatite, the latter constituting a biomaterial useful particularly in orthopedics or dentistry. The expression "injectable" pasty material is understood as meaning that the pasty material is capable of traveling through a tube appropriate to the intended application under a pressure which is non-destructive towards said material and is compatible with this application and the equipment used. The term "biomaterial" is understood in the present description as meaning the solid material obtained after hardening, this material having biocompatibility properties and being intended to replace or treat an organ or a function in humans or animals.

Calcium phosphate hydroxyapatites are well-known materials which are increasingly used in the fields of surgery and dentistry because of their biocompatibility and bone conduction properties. They can be used in dentistry for periodontal filling, the restoration of bone ridges, the filling of cysts or alveoli after dental extraction, etc., and in bone surgery for the filling of bone defects, interstitial filling between prosthesis and cortical bone, injection into bodies of vertebra, the treatment of osteoporosis, etc. The biomaterial introduced in this way may optionally contain active substances which, after hardening in situ, are slowly diffused.

These apatite biomaterials are obtained in particular by the hardening of a pasty mixture prepared by combining a mixture of calcium phosphates with water; in the applications mentioned above, the pasty mixture sets and hardens in situ at the site of application. At the present time, pasty mixtures of this type are either introduced into open sites, where they are applied by hand or with a spatula, or pushed over very short distances under high pressure into directly accessible sites. Because of their viscosity characteristics, these pasty mixtures are actually incapable of traveling under moderate pressure over distances greater than a few centimeters.

This non-injectable character limits the field of application of these materials to interventions at directly accessible sites, which do not represent the general case or entail traumatizing and complicated open surgery.

The aim of the present invention is to provide a process for the preparation of a novel injectable pasty calcium phosphate material, i.e. a material which, before it develops, can be transported under moderate pressures over considerable distances (a few tens of centimeters), said material having similar setting and hardening times to those of the existing calcium phosphate materials and producing, after hardening, an apatite biomaterial whose mechanical characteristics are comparable or superior to those of the apatite biomaterials obtained from the existing mixtures.

The process for the preparation of the injectable pasty material to which the invention relates is of the type in which water and calcium phosphates are used to produce a pasty mixture capable of developing, hardening and forming a hydroxyapatite. According to the present invention, this process comprises adding, to the calcium phosphates or the pasty mixture prior to injection, a methicone in a proportion by weight greater than 0.3% and less than 10%, and advantageously of between approximately 0.5% and 1.4%, based on the mixture. It should be remembered that methicone is a polysiloxane (belonging to the silicone family) which has a $CH_3$ group on at least one of the silicon bonds of its unit.

It has been shown experimentally that the pasty material obtained in this way is injectable and can be transported in the form of a paste through tubes of the catheter type, particularly flexible tubes, under moderate pressures (relative pressures below 1 bar) which are compatible with the conditions of surgical or dental intervention and the equipment used. This pasty material sets even in a moist environment and hardens in a similar manner to the mixture not containing methicone; however, in the absence of methicone, the mixture is impossible to inject, as is known to those skilled in the art. Furthermore, tests have made it possible to observe that the addition of methicone is capable of bringing about a significant improvement in the mechanical characteristics of the biomaterial obtained after hardening.

It should be emphasized that, in general, silicones are well-known lubricants which are used especially for coating walls so as to enable a solid or a liquid to slide along them more easily. By contrast, the methicone in the present case is intimately mixed with the pasty material and its wall-lubricating properties do not explain the injectability property which is obtained for the paste without degradation of the mechanical characteristics of the material after hardening, said characteristics even being improved. As will be seen in the Examples, wall lubrication slightly improves the ability of the paste to move over a few centimeters, but does not allow transport over a few tens of centimeters under moderate pressures (especially relative pressures below 1 bar). The injectability property obtained is difficult to explain at present: it probably involves a sliding effect between the particles, platelets and needles which form and develop during setting, this interparticulate sliding being conditioned by interfacial modifications due to the methicone; it should be pointed out, however, that the improvement in the mechanical properties obtained for the biomaterial after hardening suggests that the methicone also has a physicochemical action on the development of the material and its crystallization to apatite.

Preferably, as is known per se, the pasty mixture of calcium phosphates produced has an atomic ratio Ca/P of between 1.5 and 1.67. The biomaterial which is obtained after injection and hardening consists of a pure phase of hydroxyapatite whose chemical composition is very similar to that of the mineral part of the bone. Outside this range of atomic ratios, the biomaterial obtained is multiphase (which may be sought in certain applications).

Additives, particularly known additives for increasing the uniformity of setting of the paste (good homogeneity, absence of lumps), can be incorporated into the pasty calcium phosphate material according to the invention. For example, a water-soluble glycerophosphate, especially sodium, potassium or calcium glycerophosphate, can be added to the mixture so that the percentage by weight of this compound is less than 10%, based on the final mixture. This compound helps to improve the uniformity of setting and slightly reduces the setting rate. It should be noted that the methicone already plays a part in greatly improving the uniformity of setting of the paste and its homogeneity, so the amount of glycerophosphates can be less than that envisaged for similar mixtures not containing methicone. It should be emphasized that, in this type of cold reaction, the glycerophosphate is not decomposed and does not participate as a chemical reagent in the apatite formation reaction; the atomic ratios Ca/P are therefore given throughout the text without taking glycerophosphate into account.

The methicone used preferably has a viscosity of between approximately 20 centistokes and 500 centistokes, corresponding to a density of between approximately 0.90 and 0.98 (ratio of the density to that of water). It is advantageous to use a dimethicone containing two $CH_3$ groups on the silicon of its unit, particularly a cyclic dimethicone.

The conditions of implementation of the process of the invention can advantageously be those defined in French patent application no. 2 776 282. In one preferred mode of carrying out the process, the pasty mixture is particularly produced in the cold from a pulverulent cement of tricalcium phosphate and tetracalcium phosphate and an aqueous solution containing calcium and phosphate, the pulverulent cement and the aqueous solution being mixed at room temperature (i.e. between about 15° C. and 30° C.); the mode of implementation is preferably as follows:

preparation of the pulverulent cement by the mixing of tricalcium phosphate, tetracalcium phosphate and glycerophosphate powders, preparation of an aqueous solution of phosphoric acid and lime, and mixing of said aqueous solution and said pulverulent cement so that the overall liquid/solid weight ratio L/S is between 0.30 and 0.65 to give a homogeneous paste with an overall atomic ratio Ca/P of between 1.50 and 1.67.

This mode of implementation results in a good reproducibility of the setting and hardening and in a more coherent biomaterial (homogeneity of the product, constant setting time, absence of disintegration).

In this mode of implementation, the methicone is preferably solubilized beforehand in a solvent and the resulting liquid phase is then mixed with the pulverulent cement, after which the solvent is evaporated off to give a pulverulent cement with added dimethicone.

In practice, in the surgical or dental field, the pasty material can be made up using a kit with which the practitioners are provided, said kit comprising, in two separate containers, on the one hand a dose of pulverulent cement of tricalcium phosphate, tetracalcium phosphate and glycerophosphate, and methicone, and on the other hand a dose of aqueous solution of phosphoric acid and lime, the methicone contained in the dose of pulverulent cement being in powder form in a proportion by weight especially of between 0.3% and 2% (based on said dose of pulverulent cement). Of course, the containers containing the doses of cement and solution are sterilized after sealing.

When the intervention takes place, the practitioner opens the containers, mixes the dose of pulverulent cement and the dose of aqueous solution, homogenizes the mixture to give a paste and, before it develops, injects this paste through a tube towards the site of implantation using appropriate equipment (catheter, pump, syringe, etc.).

The dose of cement and the dose of aqueous solution are advantageously prepared according to the conditions defined below, which afford a particularly favorable compromise for medical applications of the injectable pasty material (composition of resulting hydroxyapatite very similar to that of the mineral part of the bone and tooth, setting time appropriate for the intervention—in the order of 30 minutes—, total absence of disintegration, good mechanical properties of the biomaterial obtained, etc.):

atomic ratio Ca/P of between 1.60 and 1.64, proportion by weight of glycerophosphate of between 6% and 9%, proportion by weight of methicone of between 0.5% and 1.2%, overall liquid/solid weight ratio of between 0.40 and 0.50 (the ratios and proportions indicated above referring to the final pasty mixture).

Without implying a limitation, the invention is illustrated by the following Examples with reference to the attached drawings, in which:

Figure 1:
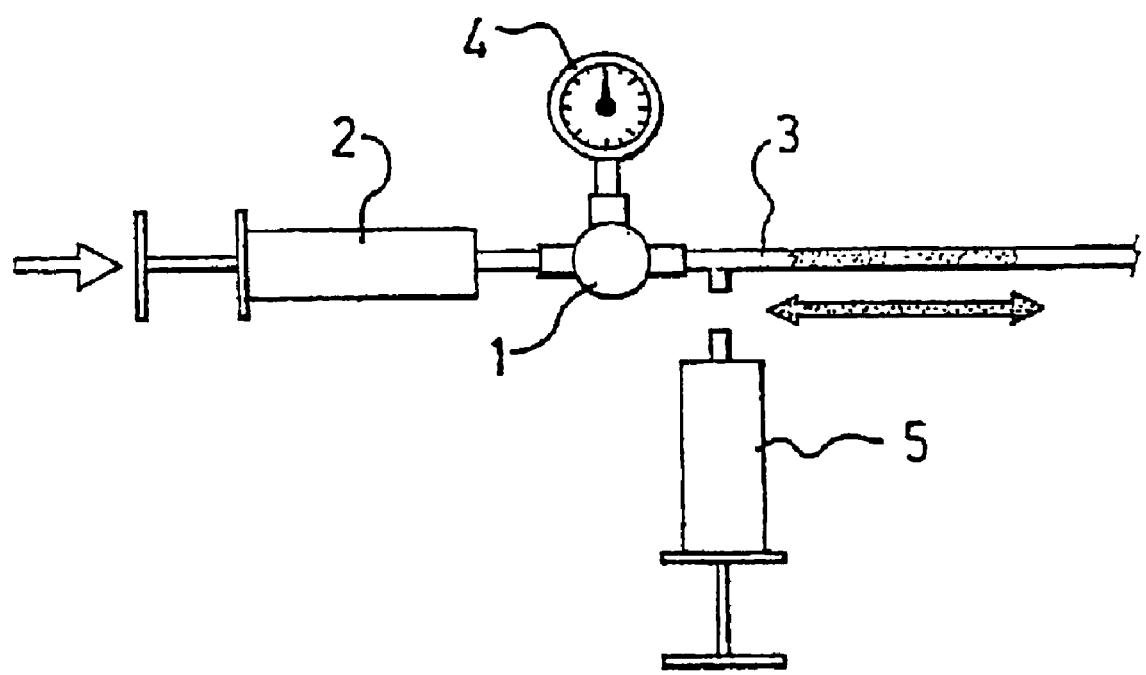
FIG. 1 is a diagram of a device for measuring the injection pressure of a pasty mixture in order to define its injectability.

The injectability of the pasty mixtures prepared in the Examples is evaluated using a system, such as that shown in FIG. 1, for exerting and measuring an injection pressure. This system is composed of a T-branch 1, a syringe 2, a catheter 3, a manometer 4 and a separate syringe 5 for introducing pasty material into the catheter 3 (temporarily separated from the T-branch).

Each series of tests is performed using identical amounts of pasty material but at different times after combination (3 min, 6 min, 10 min, 14 min, etc.).

Each amount of material is injected into the catheter 3 in the form of an 8 cm column of pasty material and the pressure required to displace this column (called the injection pressure) is measured for each test.

EXAMPLES

Example 1
Preparation of an Injectable Pasty Material in which Ca/P= 1.634, L/S=0.43, Sodium Glycerophosphate (NaGP)=6.3% and Methicone V50=0.7%

The dimethicone V50 used in Examples 1, 2 and 4 is a cyclic compound with a density of 0.92 and a viscosity of 50 centistokes.

a) A mixture of powders comprising the following constituents is prepared by accurate weighing:

tetracalcium phosphate=51.75 g, tricalcium phosphate α=38.25 g, sodium glycerophosphate=9 g.

The atomic ratio calcium/phosphorus (Ca/P) in this mixture, excluding sodium glycerophosphate, is 1.77. This mixture is homogenized, first with a mortar and then by means of a powder mixer.

A solution of dimethicone (1 g) solubilized beforehand in a small amount of cyclohexane (10 milliliters) is then added. The whole is mixed for half an hour by means of a powder mixer. This solid phase is then placed in a crystallizing dish for 72 hours to allow the solvent to evaporate off.

b) The aqueous solution of phosphate and calcium is prepared as follows:

6.25 g of phosphoric acid (density=1.69 $g/cm^3$) are added to a small amount of distilled water, and 1.646 g of calcium hydroxide are then added slowly. The solution is made up to 50 ml with distilled water to give a clear stable solution with an atomic ratio Ca/P of 0.349.

c) 7.00 g of the mixture of powders are poured into a small mortar. 3.01 g of the solution are then added with vigorous mixing using a pestle or a spatula. The mixture is pasty and homogeneous and the combination time remains fixed at 2 minutes.

The pasty material prepared by this method has an overall atomic ratio Ca/P of 1.634 and a ratio L/S of 0.43.

This material is characterized in terms of its injectability and its development.

Measurement of Injectability:

The measurements are made using the device in FIG. 1. It is found that the injection pressure remains substantially constant and low (0.7 bar) for about 11 minutes and that this pressure then increases rapidly. The material is therefore injectable for a period of 11 minutes (injectability time) without these injectability characteristics varying.

Development of the Pasty Material:

The amounts of pasty material necessary for the following tests and measurements are prepared in the same manner as above.

The development of the pasty material from a crystallographic point of view can be followed by X-ray diffraction. It is observed that the initial phases of the mixture disappear gradually and that a pure crystalline apatite phase is formed after 72 hours.

Figure 2:
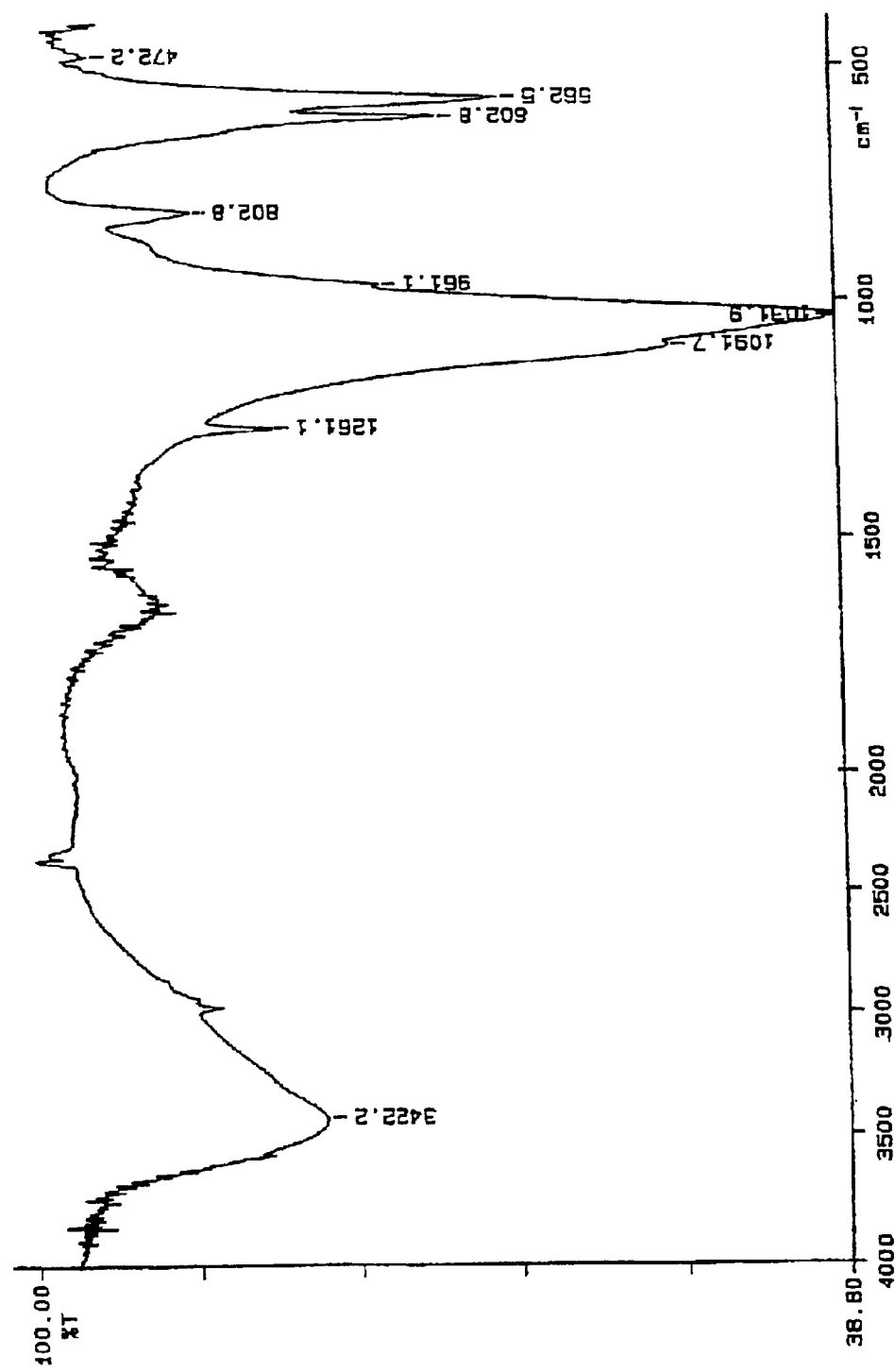
FIG. 2 is a reproduction of infrared diffraction spectra of the product obtained in Example 1 during its development (50 minutes, 60 minutes, 24 hours after combination), FIG. 3, obtained in Example 1, shows the curve representing the change in the penetration resistance of the product as a function of time.

The observation of the infrared spectra reveals the presence of silicone, a band due to silicone actually appearing at around 1260 $cm^{-1}$ (FIG. 2).

Figure 3:
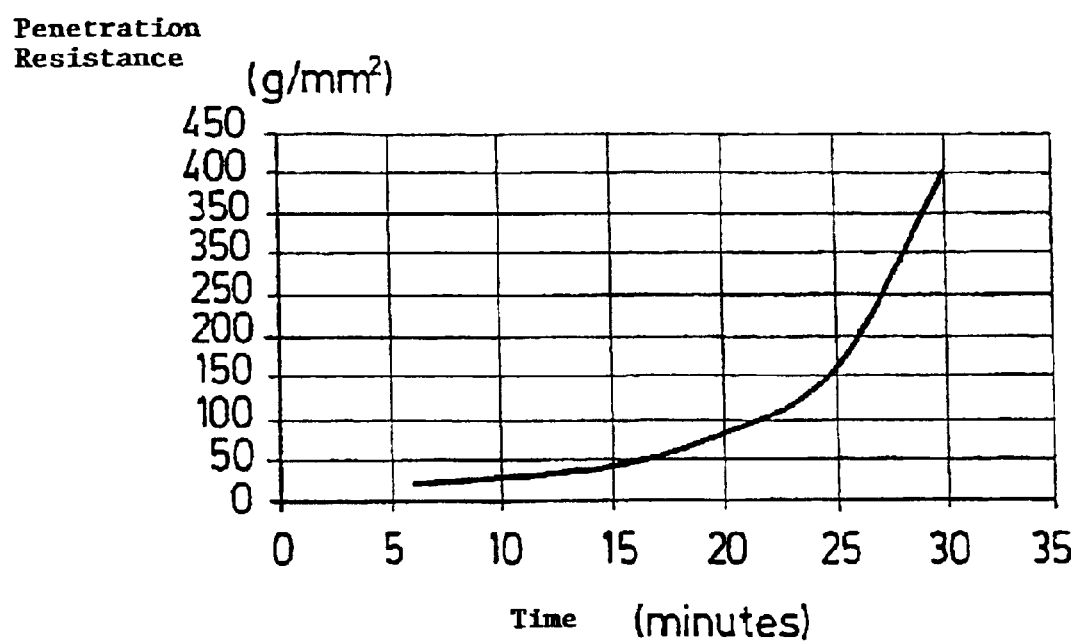

Setting Time:

Throughout the development of the mixture, the changes in plasticity are measured using a penetrometer, which measures the resistance on the surface of the pasty material to the penetration of a 1 $mm^2$ point. The curve in FIG. 3 shows the variation in this resistance as a function of time. It can be considered that the material has lost all malleability, i.e. has totally set, at a value of about 300 $g/mm^2$. Of course, it then continues to harden.

In the case of the material described, the setting value (300 $g/mm^2$) is reached after 28 minutes.

Mechanical Properties:

The mechanical properties of the biomaterials obtained from the pasty material prepared are also of interest. The compressive strength is defined on a machine of the "Hounsfield Series S" type. This is done by preparing five test pieces of the same dimensions (h=13 mm and Ø=10.6 mm) and leaving them to develop for 7 days at 37° C. in a medium of 100% humidity.

The compressive strength in this Example is 25 MPa.

Porosity:

The porosity is determined from the ratio of the experimentally calculated density (weight of the test piece divided by its volume) to the theoretical density (density of hydroxyapatite=3.15 $g/cm^3$).

The ratio of the densities is 51%, so the porosity is 49%.

Example 2

Preparation of an Injectable Pasty Material in which Ca/P=1.634, L/S=0.50, Sodium Glycerophosphate (NaGP)=6.3% and methicone V50=0.7% a) The same mixture of powders as in Example 1 (ratio Ca/P=1.77) is prepared by accurate weighing.
b) The same aqueous solution as in Example 1 is prepared to give a clear stable solution with an atomic ratio Ca/P of 0.349.
c) 7.00 g of the mixture of powders are poured into a small mortar. 3.01 g of the solution are then added, followed by 0.49 g of distilled water (to give a liquid/solid ratio of 0.50), with vigorous mixing using a pestle or a spatula. The mixture is pasty and homogeneous and the combination time remains fixed at 2 minutes.

The material prepared has an overall atomic ratio Ca/P of 1.634 and a ratio L/S of 0.50.

The injection pressure measured in this Example is 0.4 bar and the injection time is 9 minutes.

In the case of the material described, the setting value (300 $g/mm^2$) is reached after 36 minutes. The compressive strength of the biomaterial is 15 MPa and the porosity is 44%.

Example 3

Preparation of an Injectable Pasty Material in which Ca/P=1.634, L/S=0.43, Sodium Glycerophosphate (NaGP)=6.3% and Methicone V350=0.7%

The dimethicone used in this Example is a cyclic compound with a viscosity of 350 centistokes, corresponding to a density of 0.96.

a) The same mixture of powders as in Example 1 (ratio Ca/P=1.77) is prepared by accurate weighing.
b) The same aqueous solution as in Example 1 is prepared. This gives a clear stable solution with an atomic ratio Ca/P of 0.349.

The material prepared by this method has an overall atomic ratio Ca/P of 1.634 and a ratio L/S of 0.43.

As in Example 1, the same amounts are used to determine the characteristics of the material.

The injection pressure measured in this Example is 1.1 bar and the injection time is 8 minutes.

In the case of the material described here, the setting value (300 $g/mm^2$) is reached after 43 minutes. The compressive strength of the biomaterial is 25 MPa and the porosity is 47%.

Example 4

Preparation of an Injectable Pasty Material in which Ca/P=1.634, L/S=0.43, Sodium Glycerophosphate (NaGP)=7.0% and Dimethicone V50=1.75% a) A mixture of powders comprising the following constituents is prepared by accurate weighing:
   tetracalcium phosphate=50.85 g,
   tricalcium phosphate α=36.65 g,
   sodium glycerophosphate=10 g.

The atomic ratio calcium/phosphorus (Ca/P) in this mixture, excluding sodium glycerophosphate, is 1.77. This mixture is homogenized, first with a mortar and then by means of a powder mixer.

A solution of silicone (2.5 g) solubilized beforehand in a small amount of cyclohexane is then added. The whole is mixed for half an hour by means of a powder mixer. This solid phase is then placed in a crystallizing dish for 72 hours to allow the solvent to evaporate off.

b) The aqueous solution of phosphate and calcium is prepared as follows:
   6.124 g of phosphoric acid (density=1.69 $g/cm^3$) are added to a small amount of distilled water, and 1.578 g of calcium hydroxide are then added slowly. The solution is made up to 50 ml with distilled water to give a clear stable solution with an atomic ratio Ca/P of 0.341.

The material prepared by this method has an overall atomic ratio Ca/P of 1.63 and a ratio L/S of 0.43.

As in Example 1, the same amounts are used to determine the characteristics of the material.

The injection pressure measured in this Example is 0.8 bar and the injection time is 7 minutes.

In the case of the material described, the setting value (300 $g/mm^2$) is reached after 37 minutes. The compressive strength of the biomaterial is 20 MPa and the porosity is 48%.

What is claimed is:

1. A process for the preparation of an injectable pasty calcium phosphate material comprising mixing water and calcium phosphates to produce a pasty mixture, wherein a methicone in a proportion by weight of greater than 0.30% and less than 10%, based on the mixture, is added to the calcium phosphates or pasty mixture prior to injection, wherein, after injection, the paste mixture containing the methicone develops, hardens, and forms a hydroxyapatite, and wherein a water-soluble glycerophosphate is added to the pasty mixture in a proportion by weight of less than 10%, based on the mixture.

2. A process for the preparation of an injectable pasty calcium phosphate material comprising mixing water and calcium phosphates to produce a pasty mixture, wherein a methicone in a proportion by weight of greater than 0.30% and less than 10%, based on the mixture, is added to the calcium phosphates or pasty mixture prior to injection, wherein, after injection, the paste mixture containing the methicone develops, hardens, and forms a hydroxyapatite, and wherein a methicone with a viscosity of between approximately 20 and 500 centistokes is used.

3. A process for the preparation of an injectable pasty calcium phosphate material comprising mixing water and calcium phosphates to produce a pasty mixture, wherein a methicone in a proportion by weight of between approximately 0.5% and 1.4%, based on the mixture, is added to the calcium phosphates or pasty mixture prior to injection, wherein, after injection, the paste mixture containing the methicone develops, hardens, and forms a hydroxyapatite.

4. The process as claimed in claim 3, wherein a pasty mixture of calcium phosphates with an atomic ratio Ca/P of between 1.5 and 1.67 is produced.

5. The process as claimed in claim 3, wherein a methicone comprising a dimethicone containing two $CH_3$ groups on the silicon of its unit is used.

6. A process for the preparation of an injectable pasty calcium phosphate material comprising a pasty mixture, wherein the pasty mixture is produced in the cold from a pulverulent cement comprising tricalcium phosphate, tetracalcium phosphate and glycerophosphat powders, and an aqueous solution comprising a calcium compound comprising lime and a phosphate comprising phosphoric acid, mixed at room temperature, wherein a methicone in a proportion by weight of greater than 0.30%. and less than 10%, based on the mixture, is added to the calcium phosphates or pasty mixture prior to injection, wherein, after injection, the paste mixture containing the methicone develops, hardens, and forms a hydroxyapatite, and mixing said aqueous solution and said pulverulent cement so that the overall liquid/solid weight ratio is between 0.30 and 0.65 to give a homogeneous paste with an overall atomic ratio Ca/P of between 1.50 and 1.67.

7. A process for the preparation of an injectable pasty calcium phosphate material comprising mixing water and calcium phosphates to produce a pasty mixture, wherein a methicone in a proportion by weight of greater than 0.30% and less than 10%, based on the mixture, is added to the calcium phosphates or pasty mixture prior to injection, wherein, after injection, the paste mixture containing the methzcone develops, hardens, and forms a hydroxyapatite, wherein the pasty mixture is produced in the cold from a pulverulent cement comprising tricalcium phosphate and tetracalcium phosphate and an aqueous solution comprising calcium and phosphate, mixed at room temperature, and wherein the methicone is solubilized beforehand in a solvent, the resulting liquid phase is mixed with the pulverulent cement and the solvent is allowed to evaporate off.

8. The process as claimed in claim 7, further comprising preparing the pasty material which is to be injected during a surgical or dental intervention so that, after injection, it can harden in situ at the site of implantation, wherein:

a dose of pulverulent cement of tricalcium phosphate, tetracalcium phosphate and glycerophosphate, and methicone, is prepared beforehand, a dose of aqueous solution of phosphoric acid and lime is prepared beforehand, and when the intervention takes place, said dose of cement and said dose of aqueous solution are mixed and, before it develops, the mixture is injected into a tube.

9. The process as claimed in claim 8, wherein the dose of cement and the dose of aqueous solution are prepared so that the atomic ratio Ca/P in the final mixture is between 1.60 and 1.64, the proportion by weight of glycerophosphate is between 6% and 9%, based on the final mixture, the proportion by weight of methicone is between 0.5% and 1.2%, based on the final mixture, and the overall liquid/solid weight ratio is between 0.40 and 0.50.

10. A surgical or dental kit comprising, in two separate containers, a dose of pulverulent cement of tricalcium phosphate, tetracalcium phosphate and glycerophosphate in a first container, and a dose of aqueous solution of phosphoric acid and lime, in a second container, wherein the dose of pulverulent cement contains a methicone in an amount sufficient to produce an injectable pasty mixture.

11. The surgical or dental kit as claimed in claim 10, wherein the dose of pulverulent cement contains methicone in a proportion by weight of between 0.3% and 2%, based on said dose.

* * * * *